US00PP26063P3

(12) United States Plant Patent
Freyre

(10) Patent No.: US PP26,063 P3
(45) Date of Patent: Nov. 10, 2015

(54) ***RUELLIA* PLANT NAMED 'R10-105-Q54'**

(50) Latin Name: *Ruellia simplex*
Varietal Denomination: R10-105-Q54

(71) Applicant: Florida Foundation Seed Producers, Inc., Marianna, FL (US)

(72) Inventor: Rosanna Freyre, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 96 days.

(21) Appl. No.: 13/998,698

(22) Filed: Nov. 25, 2013

(65) Prior Publication Data

US 2015/0150171 P1 May 28, 2015

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

(56) References Cited

U.S. PATENT DOCUMENTS

2013/0333083 P1 12/2013 Freyre
2013/0333084 P1 12/2013 Freyre

*Primary Examiner* — Susan McCormick Ewoldt
(74) *Attorney, Agent, or Firm* — Dentons US LLP

(57) ABSTRACT

'R10-105-Q54' is a new *Ruellia* plant distinguished by having excellent landscape performance, red-violet flowers, no fruiting from selfing, low fruiting (and abortion of fruits prior to maturity) when pollinated with fertile *Ruellia* pollen, and no viable seed production, as disclosed.

3 Drawing Sheets

STATEMENT REGARDING FEDERALLY SPONSORED RESEARCH

The U.S. government has certain rights in this invention, pursuant to TSTAR Grant No. 00093296 awarded by the U.S. Department of Agriculture.

Latin name of the genus and species of the plant claimed: *Ruellia simplex.*

Variety denomination: 'R10-105-Q54'.

BACKGROUND OF THE INVENTION

The present invention relates to a new and distinct variety of *Ruellia*, botanically known as *Ruellia simplex*, and hereinafter referred to by the name 'R10-105-Q54'.

'R10-105-Q54' is an individual obtained from open-pollination of 'R10-105' grown in Citra, Fla. (North Central Florida, 29.4° N, 82.2° W, AHS heat zone 8b) in September 2012. 'R10-105' is a pink tetraploid hybrid obtained in Gainesville, Fla., which resulted from a cross between 'RU25-1'×'Chi Chi' made in September 2010. 'RU25-1' is a pink tetraploid plant, obtained as a vegetative propagule of 'RU3-25'. 'RU3-25' is a diploid-tetraploid chimeric plant obtained by treating the apical meristem of a seedling of pink *R. simplex* 'Chi Chi' with three applications, every 12 hours, of a 50 μM oryzalin solution in December 2008.

'R10-105-Q54' was first asexually reproduced in Gainesville, Fla. and has been reproduced asexually for 1 year through vegetative cuttings. The reproduced plants have been shown to retain their distinctive characteristics through successive asexual propagations.

'R10-105-Q54' has not been made publicly available more than one year prior to the filing date of this application.

BRIEF SUMMARY OF THE INVENTION

The following are the most outstanding and distinguishing characteristics of 'R10-105-Q54' when grown under normal horticultural practices in North Central and Southeastern Florida, USA:

1. Excellent performance in both full sun and partial shade environments.
2. Compact growth habit.
3. Good flowering throughout the flowering season.
4. Medium-sized red-purple flowers.
5. No fruit production from selfing.
6. Low fruit production when grown in close proximity of other *Ruellia* plants that are fertile, or when hand-pollinated with fertile *Ruellia* pollen. Fruits abort before maturity (within 14 days after pollination). Seeds are abnormal and non-viable (no germination).

BRIEF DESCRIPTION OF THE DRAWINGS

The new *Ruellia* plant is illustrated by the accompanying photographs, which show the plant's form and foliage. The colors shown are as true as can be reasonably obtained by conventional photographic procedures.

DETAILED BOTANICAL DESCRIPTION

Figure 1:
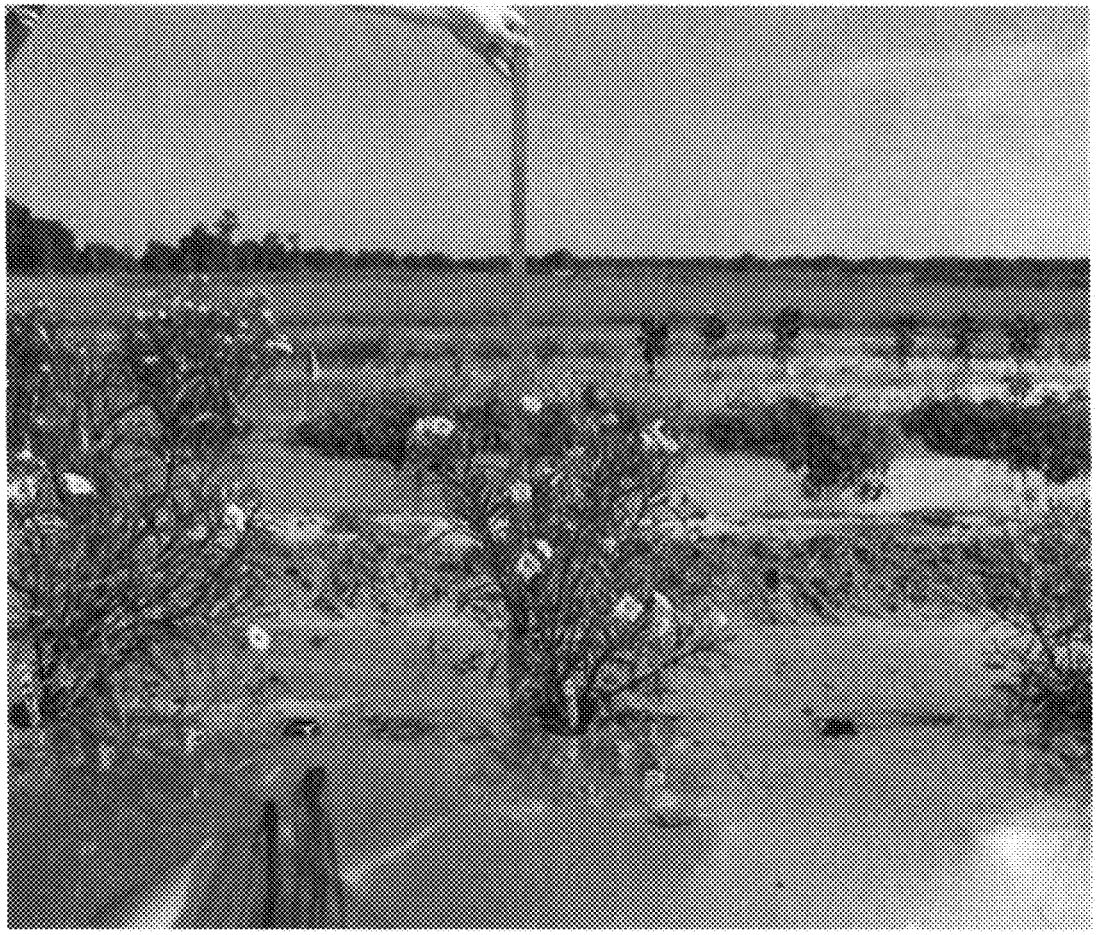
FIG. 1.—Shows 21-week-old plants of 'R10-105-Q54' on Sep. 6, 2013. Plants were grown in ground beds with drip irrigation in Citra, Fla.
Figure 2:
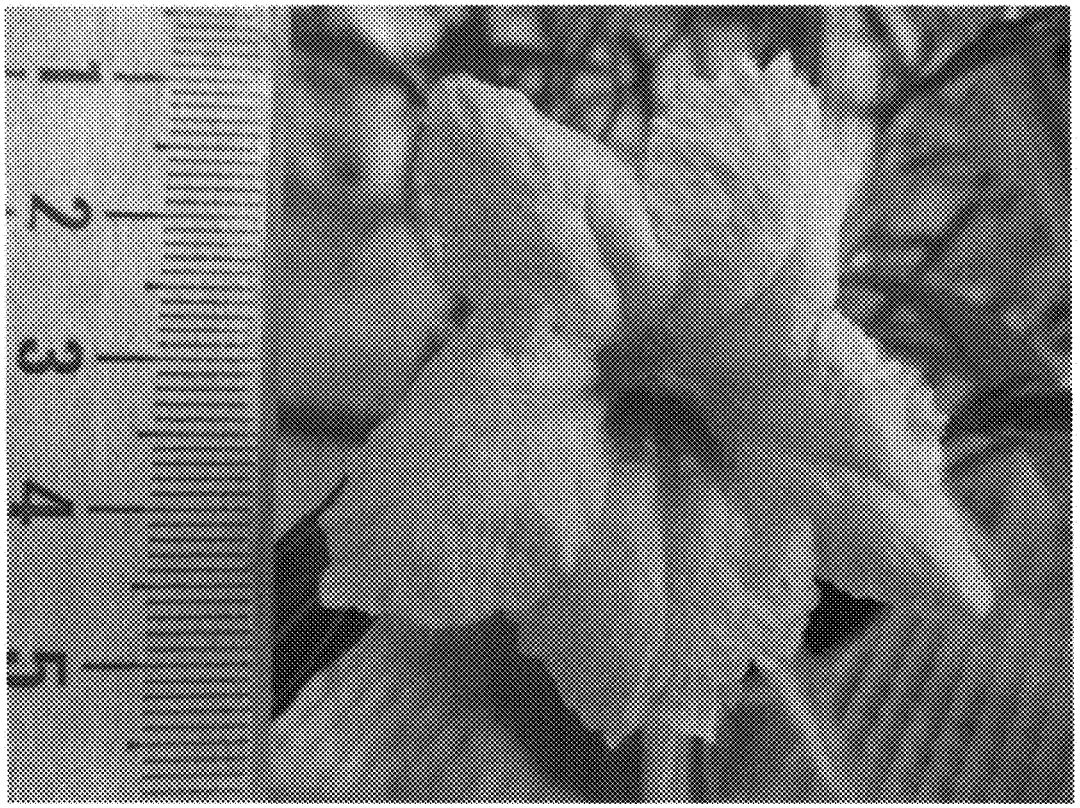
FIG. 2.—Shows a close-up of a flower of 'R10-105-Q54' on Oct. 17, 2013. Flowers shown were on a 27-week-old plant grown in a poly house in Gainesville, Fla.
Figure 3:
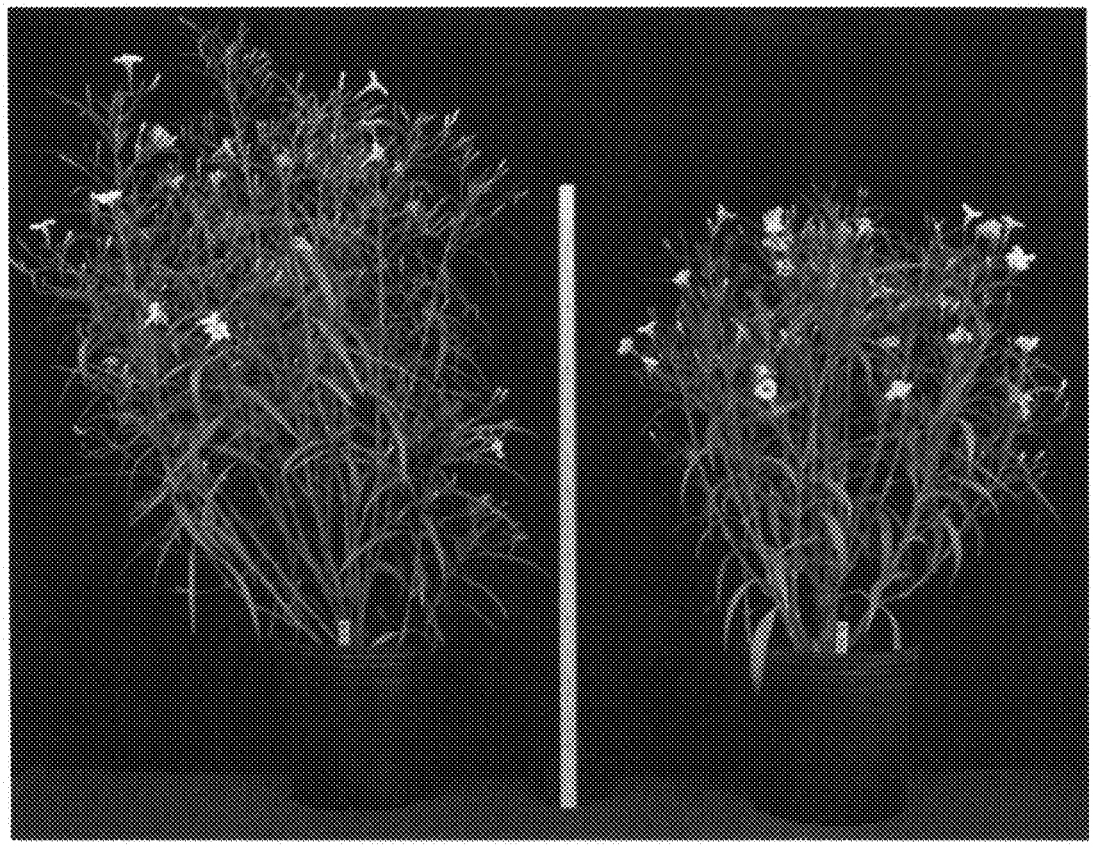
FIG. 3.—Shows 27-week-old plants of 'Chi Chi' (left) and 'R10-105-Q54' (right) on Oct. 18, 2013. Plants were grown in 11.4-L pots in a poly house in Gainesville, Fla.

The following detailed description sets forth the distinctive characteristics of 'R10-105-Q54'. The detailed description was taken on Oct. 17, 2013, which was 27 weeks after vegetative propagation from greenhouse-grown stock plants. Measurements are the means from three individual clones propagated on Apr. 10, 2013 and potted in 11.4-L pots on May 30, 2013. FAFARD® 2P mix (Agawam, Mass.; 60% Canadian peat moss, 40% perlite) was used with fertigation at 150 ppm nitrogen. Pots were placed on mesh benches in a 25% shade poly house in Gainesville, Fla. (North Central Florida, 29.7° N 82.3° W, AHS heat zone 8b).

Color references are to The R.H.S. Colour Chart of The Royal Horticultural Society of London (R.H.S.), 2001 Edition.

Phenotypic Description of *Ruellia simplex* (Variety 'R10-105-Q54')

Classification:

*Family*.—Acanthaceae.

*Botanical*.—*Ruellia simplex* hybrid.

*Common name*.—*Ruellia,* Mexican Petunia.

*Variety name*.—'R10-105-Q54'.

*Plant description*.—Form: Erect. Habit: Clumping. Height (from top of soil): 80 cm. Width (horizontal plant diameter): 64 cm.

Propagation:

*Type cuttings*.—Vegetative meristems having at least 2 nodes.

*Time to initiate roots*.—4 to 6 days.

*Time to produce a rooted cutting*.—7 to 10 days.

*Root habit*.—Adventitious (fibrous).

*Root description*.—Callus forms in 3 to 4 days; roots initiate in 5 to 8 days and become a highly branched cutting in 14 to 21 days.

Branches:

*Quantity per plant*.—9 to 11 branches per plant (with no pinching).

*Branch color*.—RHS 146B (Yellow-Green).

*Texture*.—Smooth.

*Pubescence*.—Slightly tomentose, especially at nodes.

*Stem description*.—Round to square-shaped stem, 2 cm in diameter at the soil line.

*Branch diameter*.—1 to 2 cm at the base, 0.4 at the end of a 68-cm long branch.

*Branch length*.—55 to 70 cm for first secondary branch.

*Internode length*.—6 cm.

*Anthocyanin*.—RHS 183B (Grey/Purple).

Leaves:

*Quantity of leaves per branch*.—30 (maximum, bottom leaves fall as they age).

*Arrangement*.—Decussate (opposite pairs).

*Fragrance*.—N/A.

*Shape*.—Lanceolate to elliptic.

*Length*.—15 to 17 cm (for older leaf).

*Width*.—1.5 to 3 cm.

*Apex*.—Narrowly Acute.

*Base*.—Attenuate.

*Margin*.—Entire.

*Leaf texture* (*both surfaces*).—Slightly coriaceous.

*Pubescence color* (*both surfaces*).—N/A.

*Venation color*.—Upper surface: RHS 147A (Yellow-Green). Lower surface: RHS 146B (Yellow-Green).

*Venation pattern*.—Pinnate.

*Color, mature and immature leaf*.—Upper surface: RHS 147A (Yellow-Green) (may vary depending on nutrient levels). Lower surface: RHS 146B (Yellow-Green).

*Petiole length*.—0 to 1.5 cm (absent in younger leaves).

*Petiole diameter*.—0.5 cm.

*Petiole color*.—RHS 147A (Yellow-Green).

Flowers and seeds:

*Flower* (*if present*).—Arrangement: Axillary in solitary or several-flowered cyme. Aspect: Actinomorphic corolla with 5 rounded petals; funnel form. Flowering habit (length of flowering season): May to October (N. FL). Number of inflorescences per plant: 14 to 26 cymes with 25 to 50 flowers total, plus buds. Fragrance: Very mild and slightly sweet. Lastingness of individual bloom: 1 day. Rate of opening: Daily. Flower Bud: Shape: Elliptic. Length: 2.5 cm. Diameter: 0.8 cm. Color: RHS 145B (Yellow-Green). Texture: Glandular with trichomes. Corolla: Arrangement: Actinomorphic salverform (funnel form). Length: 3 to 4 cm. Diameter: 4.5 to 5.2 cm. Color: Upper surface: RHS 66D (Red-Violet). Lower surface: RHS 65B (Red-Violet). Corolla tube: Length: 2.5 cm. Color: RHS 74A (Darker Red-Violet). Banner: Not present. Margin: Texture (both surfaces): Smooth. Shape: Undulated. Color: Upper surface: RHS 66D (Red-Violet). Lower surface: RHS 65B (Red-Violet). Keel: Not present. Calyx: Number of sepals per flower: 5. Length: 1.5 cm. Diameter: 0.4 cm. Apex: Narrowly Acute. Base: Fused. Texture (both surfaces): Smooth to glandular. Pubescence (present or absent): Present (Glandular trichomes). Sepal color: Upper surface: RHS 146B (Yellow-Green). Lower surface: RHS 146B (Yellow-Green).

*Pedicels*.—Angle: 15-25°. Length: 1.5 to 8 cm. Diameter: 0.2 cm. Texture: Smooth to glandular. Color: RHS 146B (Yellow-Green).

*Reproductive organs*.—Stamens: Present. Number: 4 anthers with stamens fused in pairs (1 long, 1 short) at base to corolla. Filament: 4 (fused). Color: RHS 155C (White). Length: 2 at 0.8 cm, and 2 at 0.5 cm. Diameter: 0.1 cm. Anther color: N/A. Pollen amount: Moderate, 10% stainable. Pollen color: RHS 155C (White). Pistils: Number/flower: 1. Pistil length: 2.2 cm. Stigma: Present. Color: RHS 155C (White). Shape: Bilabial and slightly recurved. Length: 0.2 cm. Diameter: 0.1 cm. Style: Color: RHS 155C (White). Length: 1.8 cm. Diameter: 0.1 cm. Ovary: Hypogenous. Shape: Elliptic. Color: RHS 146B (Yellow-Green).

Fruit/seed set: Very few observed, abort prior to maturity. Shape: Cylindrical capsule. Size: 1.5 to 2 cm. Color: RHS 146B (Yellow-Green). Texture: Smooth.

Disease and insect resistance: Disease and insect resistance is typical of the species.

Comparison with Parental Lines and Known Variety

Compared to the female parent 'R10-105', 'R10-105-Q54' has less fruit formation when grown in close proximity to other fertile *Ruellia*.

Twenty-one-week old 'R10-105-Q54' plants were compared to 'Chi Chi' in Citra (North Central) and Fort Pierce (South Eastern), Fla. 'R10-105-Q54' had an average height of 50 cm and width of 50 cm, while 'Chi Chi' had an average height of 62 cm width of 60 cm. Average internode lengths for 'R10-105-Q54' and 'Chi Chi' were 6 cm and 9.5 cm, respectively.

Average landscape performance rating at Citra, Fort Pierce and Gainesville, Fla. was 4.4 for 'R10-105-Q54' and 3.8 for 'Chi Chi'. Landscape performance was rated with a scale from 1-5, with 1 indicating very poor quality, not acceptable, severe leaf necrosis or chlorosis, poor form; 2 indicating poor quality, not acceptable, large areas of necrosis or chlorosis, poor form; 3 indicating acceptable quality, somewhat desirable form and color; 4 indicating very good quality, very acceptable and desirable color and form; and 5 indicating excellent quality, perfect condition, premium color and form.

Average flowering rating at Citra, Fort Pierce and Gainesville, Fla. was 3.1 for 'R10-105-Q54' and 4 for 'Chi Chi'. Flowering was rated on a 1-5 scale, with 1 indicating no flowers or buds; 2 indicating buds but no open flowers; 3 indicating 1-10 open flowers; 4 indicating 11-20 open flowers; and 5 indicating more than 20 open flowers. Corolla diameter was 4.5 to 5.2 cm for 'R10-105-Q54' and 4.8 to 5.4 for 'Chi Chi'. Colors of the upper surface of the corolla and the corolla tube were RHS 66D and RHS 74A for 'R10-105-Q54' and RHS 68D and RHS 64C for 'Chi Chi'.

Average fruiting rating at Citra, Fort Pierce and Gainesville, Fla. was 4.8 for 'R10-105-Q54' and 3 for 'Chi Chi'. Fruiting was rated on a 1-5 scale, with 1 indicating more than 50 fruits; 2 indicating 20-50 fruits; 3 indicating 10-19 fruits; 4 indicating 1-9 fruits; and 5 indicating no fruits. Fruits produced by 'Chi Chi' during 60 days in the poly house in Gainesville, Fla. were counted (120), the average number of seeds per fruit was determined (18), and the seed germination rate was calculated (82%). It was estimated that 'Chi Chi' could produce 1,766 seedlings, while 'R10-105-Q54' did not produce any fruits or seeds from selfing. When 'R10-105-Q54' was hand-pollinated with pollen from wild, purple-flowered *R. simplex,* 35% of the crosses resulted in fruit formation, and when pollinated with pink-flowered cultivar 'Chi Chi', 50% of the crosses resulted in fruit formation. However, all fruits aborted before maturation (within 14 days after pollination), and the seeds were not viable.

What is claimed is:

1. A new and distinct variety of *Ruellia* plant as shown and described herein.

* * * * *